United States Patent [19]

Sugano et al.

[11] Patent Number: 5,489,659
[45] Date of Patent: Feb. 6, 1996

[54] CATALYST COMPONENT FOR USE IN THE POLYMERIZATION OF α-OLEFINS AND PROCESS FOR PRODUCING α-OLEFIN POLYMERS USING THE SAME

[75] Inventors: Toshihiko Sugano; Toru Wada; Tomohiko Takahama, all of Yokkaichi, Japan

[73] Assignee: Mitsubishi Chemical Corporation, Tokyo, Japan

[21] Appl. No.: 198,585

[22] Filed: Feb. 18, 1994

[30] Foreign Application Priority Data

Feb. 19, 1993 [JP] Japan .................. 5-030931

[51] Int. Cl.$^6$ .................. C08F 4/64; C07F 7/02; C07F 17/00
[52] U.S. Cl. .................. 526/127; 526/126; 526/132; 526/133; 526/134; 526/160; 526/170; 526/351; 526/348.5; 556/11; 556/12; 556/43; 556/53; 556/58; 556/87; 502/103; 502/117; 502/152; 502/154; 502/155
[58] Field of Search .................. 556/11, 43, 53, 556/58, 87, 12; 502/103, 117, 152, 154, 155; 526/126, 127, 132, 133, 134, 160, 170

[56] References Cited

U.S. PATENT DOCUMENTS

| | | |
|---|---|---|
| 5,104,838 | 4/1992 | Fujita et al. . |
| 5,268,495 | 12/1993 | Riepl et al. .................. 556/11 |
| 5,314,973 | 5/1994 | Welborn, Jr. .................. 526/127 X |

FOREIGN PATENT DOCUMENTS

| | | |
|---|---|---|
| 0372414 | 6/1990 | European Pat. Off. . |
| 0529908 | 3/1993 | European Pat. Off. . |
| WO93/20113 | 10/1993 | WIPO . |

Primary Examiner—Fred Teskin
Attorney, Agent, or Firm—Oblon, Spivak, McClelland, Maier & Neustadt

[57] ABSTRACT

A catalyst component for use in the polymerization of α-olefins, comprising a compound represented by the following general formula [I]:

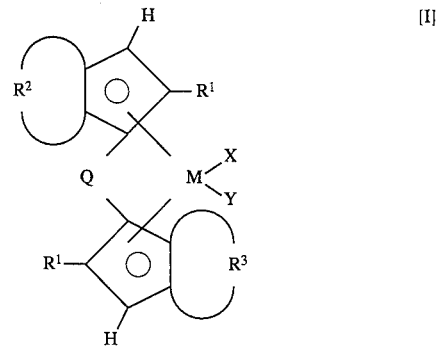

wherein $R^1$s represent a hydrogen atom, a $C_{1-6}$ hydrocarbon group or a $C_{1-12}$ hydrocarbon group containing silicon; each of $R^2$ and $R^3$ independently represents a divalent group selected from the group consisting of a hydrocarbon group having 3 to 30 carbon atoms and a silicon-containing hydrocarbon group having 1 to 30 carbon atoms and 1 to 6 silicon atoms, provided that at least one of $R^2$ and $R^3$ is said silicon-containing hydrocarbon group; Q represents a $C_{1-20}$ divalent hydrocarbon group, a silylene group, a silylene group with a $C_{1-20}$ hydrocarbon group, a germylene group, or a germylene group with a $C_{1-20}$ hydrocarbon group; X and Y represent H, a halogen, a $C_{1-20}$ hydrocarbon group, or a $C_{1-20}$ hydrocarbon group containing oxygen, nitrogen or phosphorus; and M represents a Group IVB to VIB transition metal of the Periodic Table. Production of α-olefin polymers having a high melting point and a high molecular weight in a high yield and a process for producing α-olefin polymers is made possible upon the use of the catalyst.

30 Claims, No Drawings

CATALYST COMPONENT FOR USE IN THE POLYMERIZATION OF α-OLEFINS AND PROCESS FOR PRODUCING α-OLEFIN POLYMERS USING THE SAME

BACKGROUND OF THE INVENTION

1. Field of the Invention

The present invention relates to a catalyst component for use in the polymerization of α-olefins. More specifically, the present invention relates to a catalyst component, which makes possible the production of α-olefin polymers having a high melting point, a catalyst for the polymerization of α-olefins using said catalyst component, and a process for producing α-olefin polymers using said catalyst.

2. Related Art

A so-called Kaminsky catalyst has been well known as a homogeneous catalyst for the polymerization of olefins. This catalyst is characterized in that it has a very high catalytic activity for the polymerization and can provide a polymer with a narrow molecular weight distribution.

As transition metal compounds useful for the production of isotactic polyolefins by Kaminsky catalyst, ethylenebis(indenyl)zirconium dichloride and ethylenebis (4,5,6,7-tetrahydroindenyl)zirconium dichloride (Japanese Patent Laid-Open Publication No. 130314/1986) have been known. They, however, have disadvantages including that the resultant polyolefins have a low molecular weight and polymerization at a low temperature can provide high-molecular weight polyolefins only at the sacrifice of the polymerization activity of the catalyst. Further, it has been known that a high-molecular weight polymer can be produced when a hafnium compound is used instead of zirconium as a transition metal compound (Journal of Molecular Catalysis, 56 (1989) p. 237–247). However, this method may, to the best of our knowledge, have a shortcoming in that the polymerization activity is low.

Furthermore, dimethylsilylbis-substituted cyclopentadienylzirconium dichloride and the like are proposed in Japanese Patent Laid-Open Publication No. 301704/1989, Polymer Preprints, Japan Vol. 39, No. 6, p. 1614–1616 (1990) and Japanese Patent Laid-Open Publication No. 124406/1991, and dimethylsilylenebis(indenyl)zirconium dichloride and the like are proposed in Japanese Patent Laid-Open Publication Nos. 295007/1988 and 275609/1989. These proposals may have made possible the production of polymers having a high stereoregularity and a high melting point by polymerization at relatively low temperatures. To the best of our knowledge, however, a lowering in the stereoregularity, melting point and molecular weight of the polymers would be significant when the polymerization is carried out under high temperature conditions that are favorable from the viewpoint of economy.

Japanese Patent Laid-Open Publication Nos. 268307/1992 and 268308/1992 suggest that the stereoregularity and molecular weight can be improved to some extent when use is made of cyclopentadienyl compounds as referred to above which have a substituent to the position (2-position) adjacent to the crosslinking group in the cyclopentadienyl compounds. This method, however, would still be unsatisfactory in the performance under polymerization conditions of an increased polymerization temperature regarded as advantageous from the viewpoint of economy.

An object of the present invention is to provide a catalyst component for the polymerization of α-olefins, by which catalyst extrudable and injection-moldable olefin polymers having a high molecular weight and a high melting point can be obtained in a high yield, a catalyst for the polymerization of α-olefins and a process for producing α-olefin polymers.

SUMMARY OF THE INVENTION

The present invention has been made as a result of studies with a view to solving the above-described problem.

More specifically, the present invention provides a component of a catalyst for the polymerization of α-olefins which comprises a compound represented by the following general formula [I]:

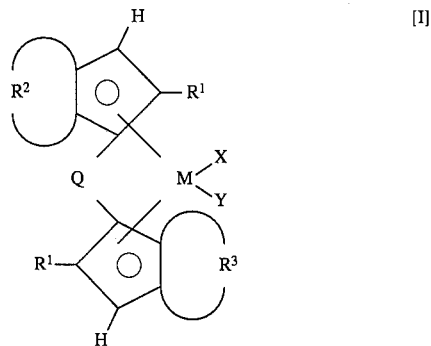

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent group selected from the group consisting of a hydrocarbon group having 3 to 30 carbon atoms and a silicon-containing hydrocarbon group having 1 to 30 carbon atoms and 1 to 6 silicon atoms, provided that at least one of $R^2$ and $R^3$ is said silicon-containing hydrocarbon group; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table.

Further, the present invention relates to a catalyst for the polymerization of α-olefins, comprising the above-described catalyst component.

More specifically, the catalyst for the polymerization of α-olefins according to the present invention comprises in combination:

Component (A) which is a catalyst component for the polymerization of α-olefins, comprising a compound represented by the following general formula [I]:

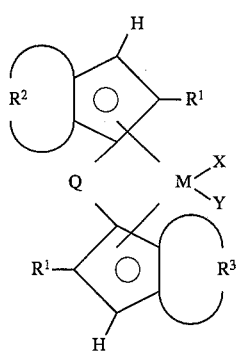

wherein R¹s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent group selected from the group consisting of a hydrocarbon group having 3 to 30 carbon atoms and a silicon-containing hydrocarbon group having 1 to 30 carbon atoms and 1 to 6 silicon atoms, provided that at least one of $R^2$ and $R^3$ is said silicon-containing hydrocarbon group; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table; and Component (B): (i) an aluminum oxy compound, (ii) a Lewis acid or (iii) an ionic compound which can react with Component (A) to convert Component (A) to a cation.

Further, the present invention relates to a process for producing an α-olefin polymer wherein use is made of the above-described catalyst.

More specifically, the process for producing an α-olefin polymer according to the present invention comprises contacting an α-olefin with a catalyst comprising in combination:

Component (A) which is compound of a catalyst component for the polymerization of α-olefins, comprising a compound represented by the following general formula [I]:

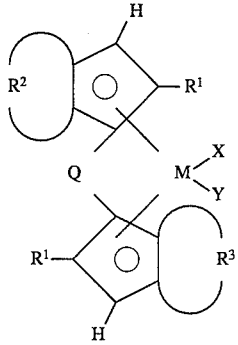

wherein R¹s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent group selected from the group consisting of a hydrocarbon group having 3 to 30 carbon atoms and a silicon-containing hydrocarbon group having 1 to 30 carbon atoms and 1 to 6 silicon atoms, provided that at least one of $R^2$ and $R^3$ is said silicon-containing hydrocarbon group; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table; and Component (B) which is (i) an aluminum oxy compound, (ii) a Lewis acid or (iii) an ionic compound which can react with Component (A) to convert Component (A) to a cation.

By the use of the catalyst according to the present invention, the production of α-olefin polymers having a high melting point and a high molecular weight in a high yield becomes possible.

The mechanism through which the effect or advantage inherent in the present invention are developed has not been elucidated yet, but it is believed to be as follows although it is to be noted that the present invention is not bound by the following mechanism. In contrast to a known fused ring in the art which is an indenyl group or a 4,5,6,7-tetrahydroindenyl group, the fused ring in the present invention which has a silicon-containing hydrocarbon ring fused with a cyclopentadienyl ring may be characterized by the fact that the fused ring has higher steric hindrance effect on the metal M in the formula [I] since, when the silicon atom is a ring member of the ring formed by $R^2/R^3$ fused with the cyclopentadiene ring, the ring formed by $R^2/R^3$ has a slightly bigger size than a ring with no Si atom as a ring member due to the length of a Si-C bond which is slightly longer than the length of a C-C bond, and since, when the silicon atom is pendent from the ring formed by $R^2/R^3$, the pendent Si atom may protrude from the ring. The steric hindrance generated by the Si-containing $R^2$ and/or $R^3$ against the metal M is assumed to improve the stereoregulating capability of the catalyst, and the capability may be preserved at a high level even at an elevated temperature for polymerization since the stereostructure of the fused ring may still be preserved. Further, the stereostructure of the catalyst component in the present invention may prevent withdrawal of the β-hydrogen which has in the art been considered to cause molecular weight lowering due to the chain transfer.

The above-described effect is considered unexpectable from the conventional techniques.

DETAILED DESCRIPTION OF THE PREFERRED EMBODIMENTS OF THE INVENTION

The present invention relates to a polymerization catalyst component, which comprises a compound which is described below as Component (A). The present invention relates further to a catalyst for the polymerization of α-olefins, which comprises Component (A) and Component (B) which will be described in more detail, and still further to a process for producing an α-olefin polymer, which comprises contacting an α-olefin with a catalyst comprising this catalyst. The expressions "comprises" herein is intended to mean that the given specified compounds or components or steps can be used in combination with other compounds or components or steps as long as the additional compounds and components are not detrimental to the effect of the present invention.

<Component (A)>

The catalyst component (A) of the present invention comprises a transition metal compound represented by the following general formula [I]:

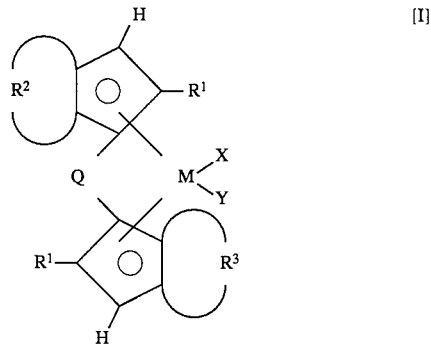

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent group selected from the group consisting of a hydrocarbon group having 3 to 30 carbon atoms and a silicon-containing hydrocarbon group having 1 to 30 carbon atoms and 1 to 6 silicon atoms, provided that at least one of $R^2$ and $R^3$ is said silicon-containing hydrocarbon group; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table.

The metallocene compound represented by formula [I] used in the present invention has a significant feature in that two five-membered cyclic ligands having the substituents $R^1$, $R^2$ and $R^3$ are asymmetric about a plane containing M, X and Y when viewed from their relative position in terms of the group Q.

As described above, $R^1$ is a hydrogen atom, a hydrocarbon group having 1 to 6 carbon atoms or a hydrocarbon group having 1 to 12 ,carbon atoms with a silicon atom contained therein. More specifically, $R^1$ is a hydrogen atom, a saturated hydrocarbon group-such as alkyl or cycloalkyl, an unsaturated hydrocarbon group such as vinyl or alkenyl, or a silicon-containing hydrocarbon group such as alkylsilyl. Specific examples of $R^1$ include methyl, ethyl, n-propyl, i-propyl, n-butyl, i-butyl, t-butyl, n-amyl, i-amyl, n-hexyl, cyclocyclopropyl, allyl, trimethylsilyl and dimethylethylsilyl groups. Of these groups, alkyl groups having 1 to 4 carbon atoms such as methyl, ethyl, n-propyl, i-propyl, cyclopropyl, n-butyl, i-butyl and t-butyl are preferred.

$R^2$ and $R^3$ each represent independently a divalent hydrocarbon group having 3 to 30 carbon atoms or a divalent silicon-containing group having 1 to 30 carbon atoms and 1 to 6 silicon atoms. Since these groups are divalent, $R^2$ and $R^3$ are each in the form of a ring condensed with the five-membered/cyclopentadienyl ring, and, when they represent "silicon-containing hydrocarbon group", the silicon-containing hydrocarbon group includes the case where the silicon is a member of the ring and the case where the silicon is pendent from the ring as, for example, a trimethylsilyl group. In either case, the remaining valence of the silicon atom, viz. typically two for the former case or three for the latter case, may be a hydrocarbon group of 1 to 10, preferably 1 to 8, carbon atoms, a lower alkyl of 1 to 4 carbon atoms such as methyl being more preferable. $R^2$ and $R^3$ should meet another requirement that at least one of the ring formed therewith (fused with the cyclopentadiene ring) be the very divalent silicon-containing hydrocarbon group, namely that of 1 to 30 carbon atoms and of 1 to 6 silicon atoms. Preferable examples of the silicon-containing hydrocarbon group include those which form a five- or higher membered ring fused with the cyclopentadiene group sharing two carbon atoms of the cyclopentadiene group, wherein the total of silicon and carbon atoms in $R^2/R^3$ should thus be at least 3.

$R^2$ and $R^3$ can have a multi-ring structure such that the ring formed therewith which is fused with the cyclopentadiene ring has a further ring fused therewith. The further ring condensed, which may be called "a daughter ring condensed" in reference to the ring with which the daughter ring is condensed and which is condensed with the cyclopentadiene group and is called "a parent ring condensed", should form a "bridge" composed of at least one methylene group, which bridge can be formed between the adjacent carbon atoms in the parent ring or between the non-adjacent carbon atoms. The daughter ring may or may not be on the plane of the parent ring, the latter being preferable.

Examples of $R^2$ and $R^3$ include:

(1) a divalent saturated hydrocarbon group, including an alkylene and a cycloalkylene such as n-butylene, 1-methylbutylene, 2-methylbutylene, 1,2-dimethylbutylene, 1-cyclopropylbutylene and 1-phenylbutylene;

(2) a divalent unsaturated hydrocarbon group, including an alkenylene, an alkadienylene and arylene, such as 2-methyl-1,3-butadienylene, 2-phenyl-1,3butadienylene, 1-pentenylene, 1,3-pentadienylene, 1,4-pentadienylene, 3-methyl-1,4-pentadienylene, 1-methyl-2,4-pentadienylene, 1,3-hexadienylene, 3,4-dimethyl-1,5-hexadienylene, 1,3,5-hexatrienylene;

(3) a silicon-containing, saturated hydrocarbon group, including an alkylsilylene and an alkylsilylalkylene, such as 1-trimethylsilylbutylene, 1-dimethylethylsilylbutylene, dimethylsilylenepropylene, ethyl-1,2-bisdimethylsilylene, propyl-1,3-bisdimethylsilylene, and dimethylsilanediethylene;

(4) a silicon-containing, unsaturated hydrocarbon group, including alkylsilylalkenylene, an alkylsilylalkadienylene and an alkylsilylarylene, such as 2-trimethylsilyl-1,3-butadienylene, 3-trimethylsilyl- 1,4-pentadienylene, 5-trimethylsilyl- 1,3-pentadienylene; and (5) a polycyclic, silicon-free or silicon-containing, saturated or unsaturated hydrocarbon group, such as cyclopentanylene, dimethylcyclopentanylene, 1,1-dimethylcyclobutane- 2-methylene and cyclohexanylene.

Q is a divalent group or a bridge which crosslinks the two conjugated five-membered cyclic ligands, and examples thereof include (i) a divalent hydrocarbon group having 1 to 20 carbon atoms, preferably 1 to 6 carbon atoms, more specifically, for example, a saturated hydrocarbon group such as an alkylene, cycloalkylene, arylene group, (ii) a silylene group, (iii) a silylene group with a hydrocarbyl substituent thereon having 1 to 20 carbon atoms, preferably 1 to 12 carbon atoms, (iv) a germylene group, or (v) a germylene group with a hydrocarbyl substituent thereon having 1 to 20 carbon atoms, preferably 1 to 12 carbon atoms. Of these groups, alkylene, cycloalkylene, arylene and alkylsilylene groups are preferred, an alkylene or alkylsilylene group being more preferable. The bond-to-bond distance or the "span of bridge" of the divalent Q group is, irrespective of the total number of carbon atoms contained therein, such that when Q is in a chain form, it is preferably about 4 or less atoms, especially 3 or less atoms, while when Q has a cyclic group, it is preferably the cyclic group + about two atoms or shorter, especially the cyclic group alone. Therefore, when Q is an alkylene, the alkylene is preferably ethylene and isopropylidene, ethylene being more preferable, wherein the bond-to-bond distance is of two atoms and one atom, respectively; when Q is a cycloalkylene, the cycloalkylene is preferably cyclohexylene, wherein the bond-to-bond distance is one cyclic group, i.e., the cyclohexylene group alone; and when Q is an alkylsilylene, the alkylsilylene is preferably dimethylsilylene, wherein the bond-to-bond distance is one atom, namely a silicon atom.

X and Y each independently, i.e., which may be the same or different, represent (i) a hydrogen atom, (ii) a halogen atom, e.g., a fluorine, chloride, bromine or iodine atom, preferably a chlorine atom, (iii) a hydrocarbon group having 1 to 20 carbon atoms or (iv) a hydrocarbon group having 1 to 20 carbon atoms and containing an oxygen atom, preferably an alkoxy group having 1 to 10 carbon atoms, a nitrogen atom, preferably an amino group having 1 to 12 carbon atoms, a silicon atom, preferably a siloxy group having 1 to 18 carbon atoms or a phosphorus atom, preferably a phosphine group having 1 to 12 carbon atoms.

M is a Group IVB to VIB transition metal of the Periodic Table, preferably a group IVB transition metal, i.e., titanium, zirconium or hafnium, still preferably zirconium.

The compound [I] of the present invention can be synthesized by any method suitable for forming any substituent or bond desired of the compound. One representative synthesis route is as follows. In the following scheme, $HR^a$ represents a compound represented by the following formula:

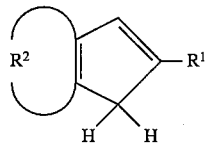

$HR^a + n\text{-}C_4H_9Li \rightarrow R^aLi + n\text{-}C_4H_{10}$
$2R^aLi + QCl_2 \rightarrow Q(R^a)_2 + 2LiCl$
$Q(R^a)_2 + 2 \cdot n\text{-}C_4H_9Li \rightarrow (R^bLi)_2 + 2 \cdot n\text{-}C_4H_{10}$
(wherein $HR^b = R^a$)
$Q(R^bLi)_2 + ZrCl_4 \rightarrow Q(R^b)_2ZrCl_2 + 2LiCl$ Nonlimitative examples of the above-described transition metal compound are as follows. It is to be noted that although the compounds listed below are described simply by their chemical names, they are, as a matter of course, asymmetric in stereostructure as defined previously.

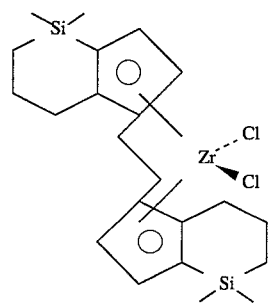 (1)

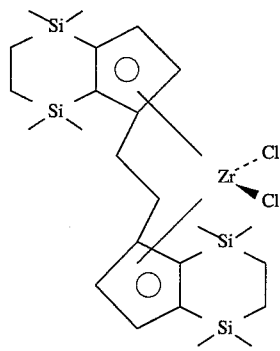 (2)

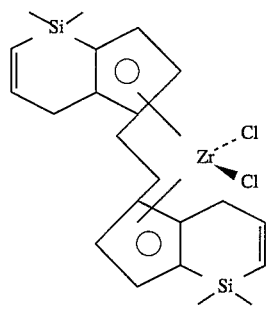 (3)

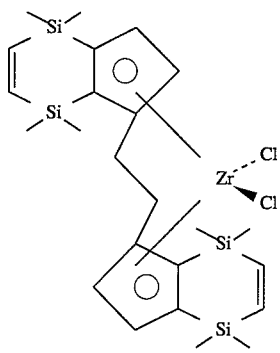 (4)

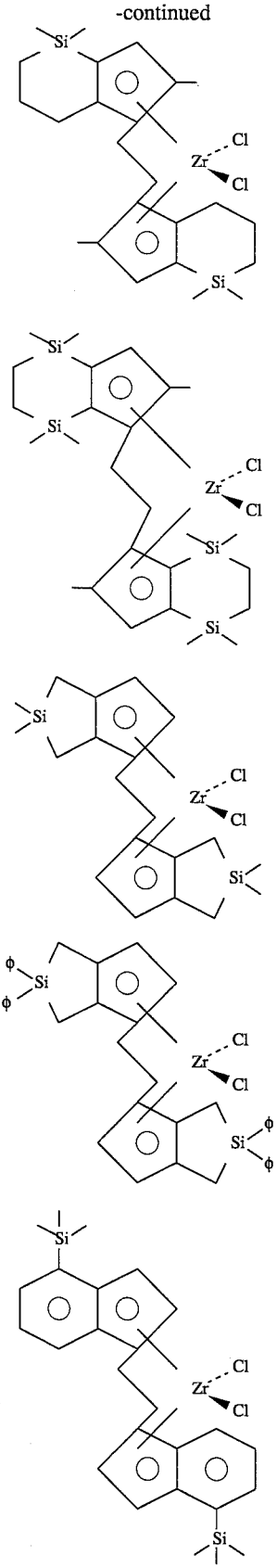
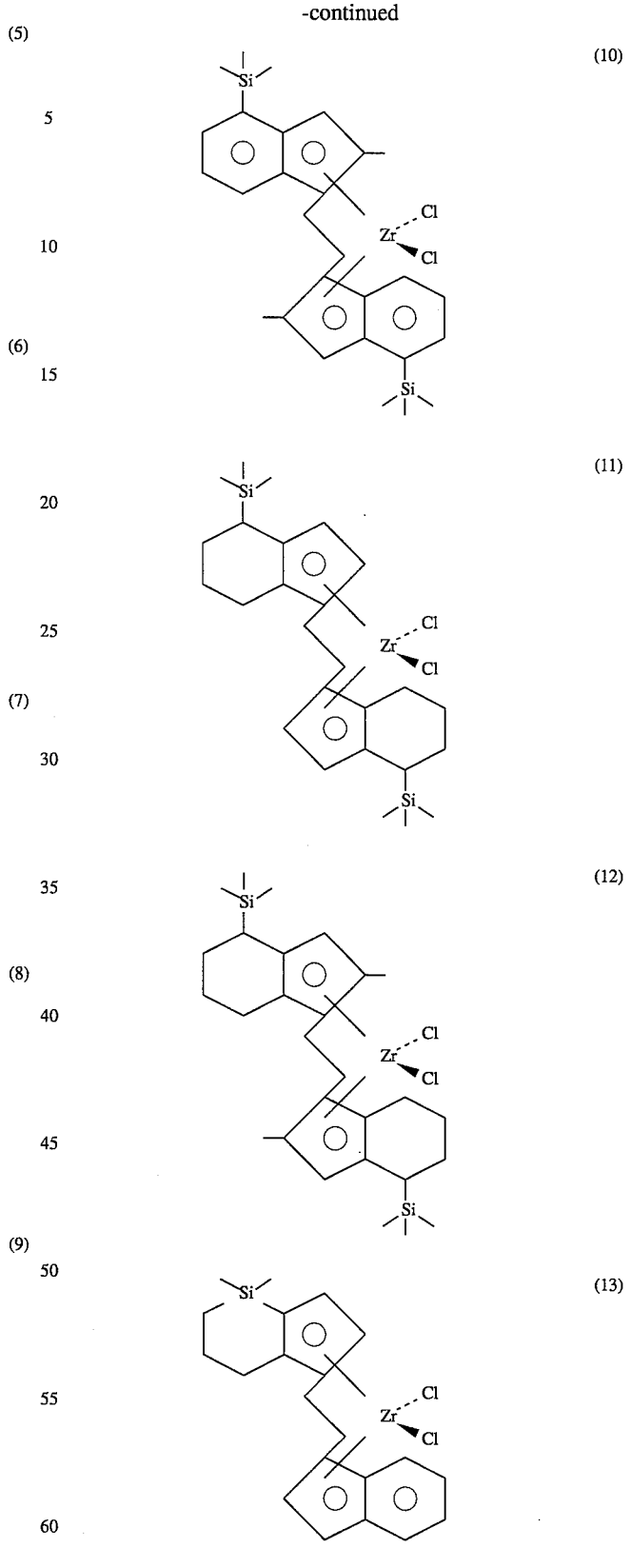

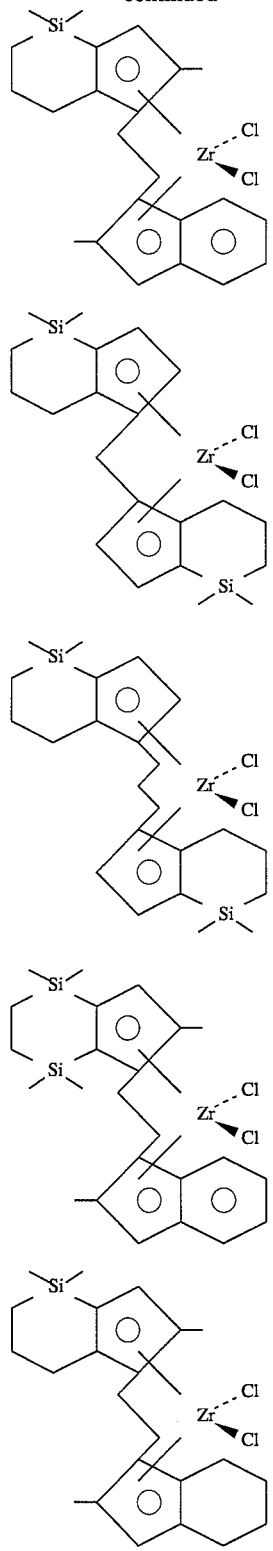
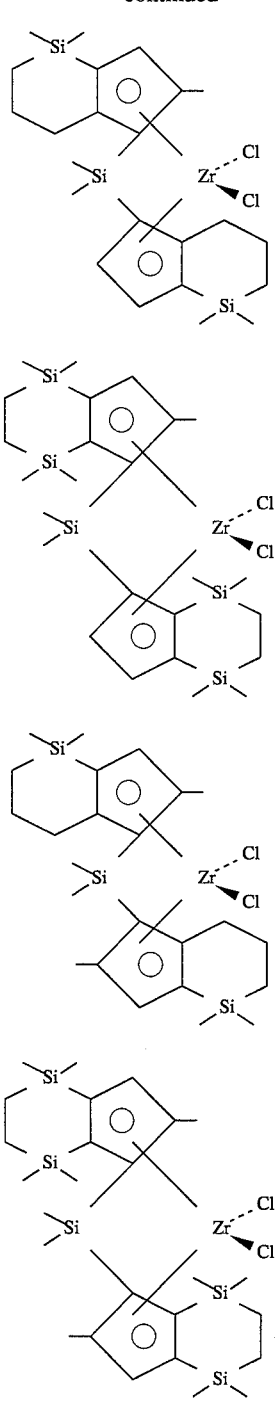

(23)
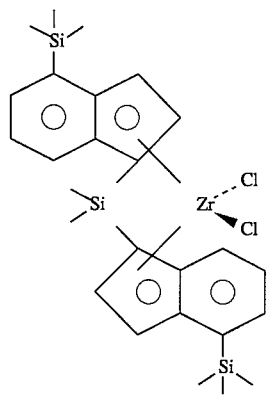
(24)
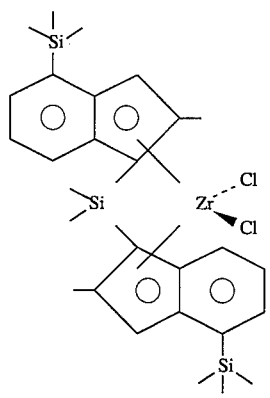
(25)
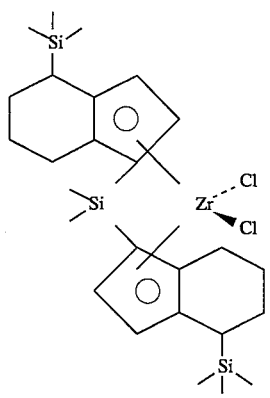
(26)
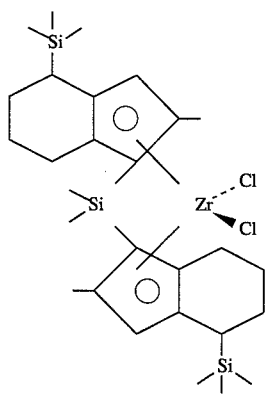
(27)
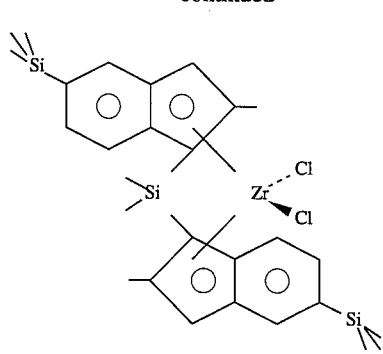
(28)
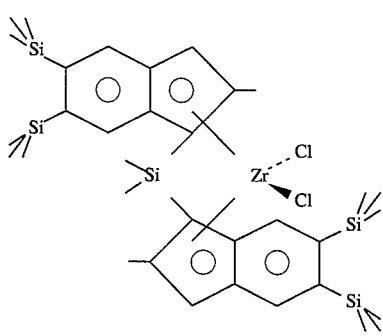
(29)
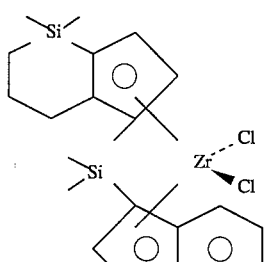
(30)
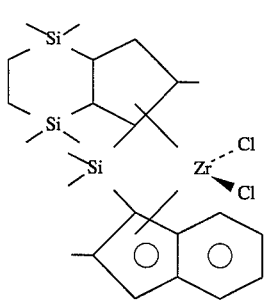
(31)
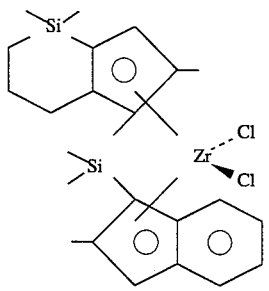

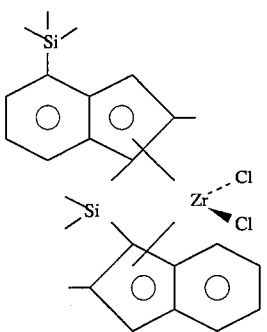
(32)
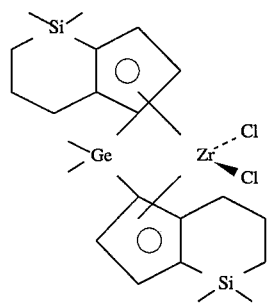
(37)
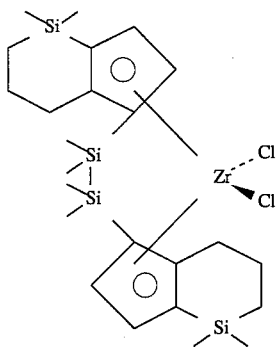
(33)
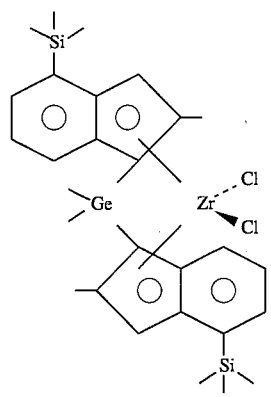
(38)
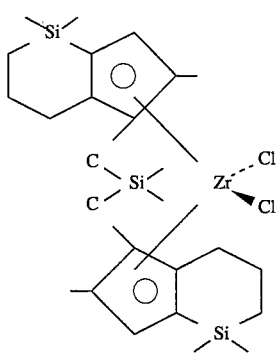
(34)
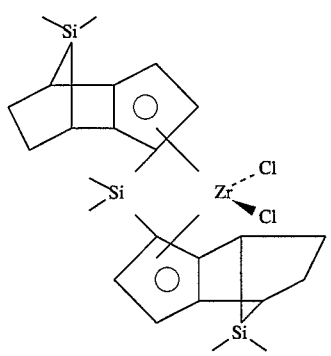
(39)
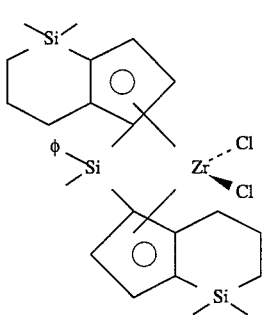
(35)
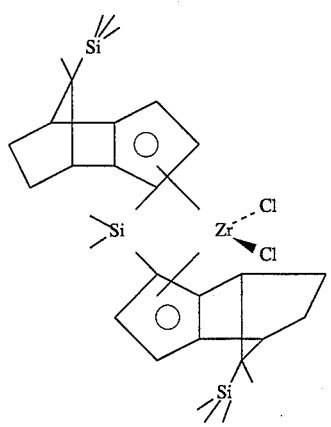
(40)
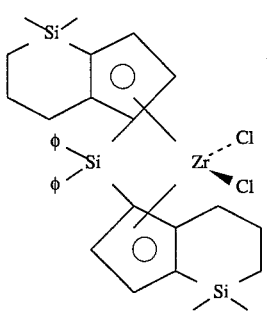
(36)

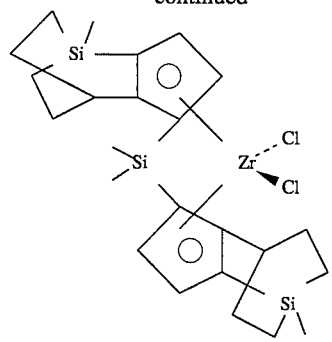 (41)
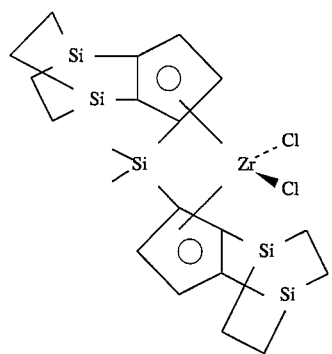 (42)
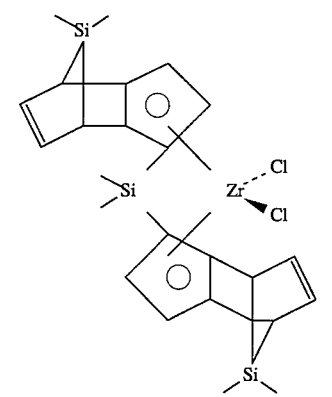 (43)
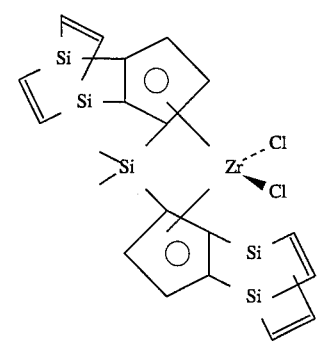 (44)
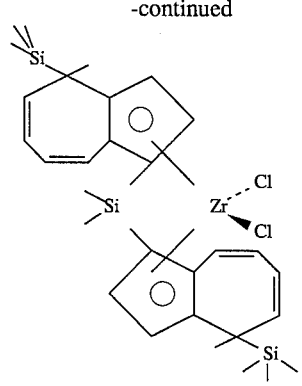 (45)
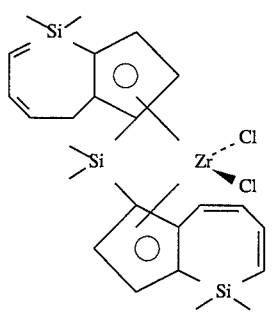 (46)
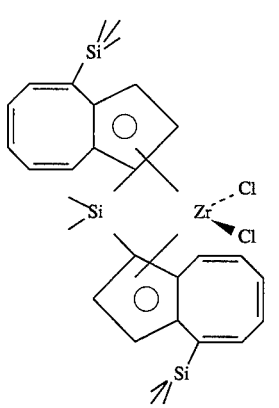 (47)
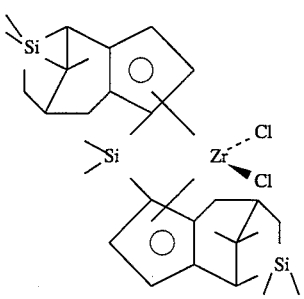 (48)

Further examples of the transition-metal compound include compounds wherein one or both of the chlorides of the above-described compounds are replaced with a bromine, iodine, or hydrogen atom, or a methyl, phenyl, or benzyl group, or an alkoxy group. Still further examples of the transition-metal compound include compounds wherein the zirconium atom of the above-described compounds is replaced with a titanium, hafnium, tantalum, niobium, vanadium, tungsten, or molybdenum atom. Of these compounds, compounds of the Group IVB transition metals, i.e., titanium, zirconium and hafnium, are preferred. Still preferred compounds are those wherein M is zirconium. Particularly preferred are compounds having as a ligand a fused ring where the silicon atom inherent in the moiety $R^2/R^3$ is a member of the ring formed with the $R^2/R^3$ and fused with the cyclopentadiene, such as (a) the compound Nos. (1) to (6), (13) to (22), (29) to (31), (33) to (37), (41) to (42), (44) and (46), and such derivatives of these compounds (a) that (b-1) the transition metal Zr has been replaced by Ti or Hf or that (b-2) the chlorine atom attaching to the transition metal has been replaced by a substituent selected from the group consisting of a hydrogen atom, an alkyl group of 1 to 6 carbon atoms, an alkoxy group of 1 to 6 carbon atoms, an alkylamido group of an alkyl of 1 to 6 carbon atoms, a siloxy group, and an alkylphosphino group of an alkyl of 1 to 6 carbon atoms, particularly those where the chlorine atom attaching to Zr has been replaced by methyl, ethyl, benzyl, dimethylamido, diethylamido or trimethylsiloxy group. The compounds (a) given above are preferable.

Still more preferable compounds of the formula [I] are further restricted compounds of those enumerated hereinabove, viz. compounds (a) and compounds (b-1) and (b-2), in that the five-membered ring has a substituent at its 2-position, preferable examples including the compound Nos. (5), (6), (14), (17), (18), (21), (22), (30), (31) and (34).

<Component (B)>

Component (B) is (i) an aluminum oxy compound, (ii) a Lewis acid or (iii) an ionic compound which can react with Component (A) to convert Component (A) to a cation.

Some Lewis acids can also be regarded as an "ionic compound which can react with Component (A) to convert Component (A) to a cation". Therefore, compounds belonging to both the "Lewis acid" and the "ionic compound which can react with Component (A) to convert Component (A) to a cation" are interpreted as those belonging to any one of these groups.

Specific examples of the aluminum oxy compound include compounds represented by the following general formulae [II], [III] and [IV]:

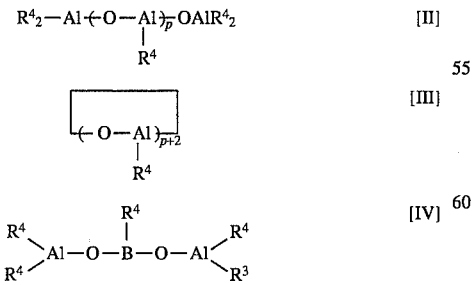

wherein p is a number of 0 to 40, preferably 2 to 30, $R^4$ is hydrogen, a hydrocarbon group or a halogen-containing hydrocarbon group, preferably a hydrocarbon group having 1 to 10 carbon atoms or a halogen-containing hydrocarbon group having 1 to 10 carbon atoms, particularly preferably 1 to 6 carbon atoms.

The compounds represented by the general formulae [II] and [III] are called "alumoxane" that is a product of a reaction of one species of a trialkylaluminum or two or more species of a trialkylaluminums with water. Specific examples of the alumoxanes include (i) alumoxanes obtained from one species of a trialkylaluminum and water, that is, methylalumoxane, ethylalumoxane, propylalumoxane, butylalumoxane and isobutylalumoxane and (ii) alumoxanes obtained from two species of a trialkylaluminum and water, that is, methylethylalumoxane, methylbutylalumoxane, methylisobutylalumoxane, etc. Of these compounds, methylalumoxane and methylisobutylalumoxane are particularly preferred.

It is also possible to use a plurality of alumoxanes selected within and/or between the above groups (i) and (ii). Moreover, the above alumoxanes can be used in combination with another alkylaluminum compound such as trimethylaluminum, triethylaluminum, triisobutylaluminum or dimethylaluminum chloride.

The above alumoxanes can be prepared under the various known conditions. Specifically, the following methods may be mentioned:

(a) the method in which a trialkylaluminum is directly reacted with water in an appropriate organic solvent such as toluene, benzene or ether;

(b) the method in which a trialkylaluminum is reacted with a salt hydrate containing water of crystallization, such as a hydrate of copper sulfate or of aluminum sulfate;

(c) the method in which a trialkylaluminum is reacted with water having impregnated silica gel or the like;

(d) the method in which trimethylaluminum and triisobutylaluminum are mixed and the mixture is directly reacted with water in an appropriate organic solvent such as toluene, benzene, or ether;

(e) the method in which trimethylaluminum and triisobutylaluminum are mixed, and the mixture is reacted, while heating, with a salt hydrate containing water of crystallization, such as a hydrate of copper sulfate or of aluminum sulfate;

(f) the method in which silica gel or the like that has been impregnated with water in advance is treated with triisobutylaluminum, and then subjected to an additional treatment with trimethylaluminum;

(g) the method in which methylalumoxane and isobutylalumoxane are synthesized separately by the known methods, mixed in the predetermined amounts, and reacted with each other while heating; and (h) the method in which a salt containing water of crystallization such as $CuSO_4 \cdot 5H_2O$ is added to an aromatic hydrocarbon solvent such as benzene or toluene, and reacted with trimethylaluminum at a temperature of approximately −40° C. to 40° C. The amount of water used in these methods, in general, is from 0.5 to 1.5 when expressed by the molar ratio to the trimethylaluminum. The methylalumoxane thus obtained is a linear [II] or cyclic [III] organoaluminum polymer.

The compound represented by the general formula [IV] can be prepared by a reaction between one species of a trialkylaluminum or two or more species of a trialkylaluminums and an alkylboronic acid:

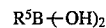

wherein $R^5$ represents an alkyl group having 1 to 10 carbon atoms, preferably 1 to 6 carbon atoms, in a molar ratio of 10:1 to 1:1. Specific examples of the compound include (i) a product of a reaction between trimethylaluminum and methylboronic acid in a ratio of 2:1, (ii) a product of a reaction between triisobutylaluminum and methylboronic acid in a ratio of 2:1,. (iii) a product of a reaction among trimethylaluminum, triisobutylaluminum and methylboronic acid in a ratio of 1:1:1, (iv) a product of a reaction between trimethylaluminum and ethylboronic acid in a ratio of 2:1 and (v) a product of a reaction between triethylaluminum and butylboronic acid in a ratio of 2:1. These compounds represented by the general formula [IV] may be used in combination of two or more thereof. Further, it is also possible to use the compounds represented by the general formula [IV] in combination with an alumoxane represented by the general formula [II] or [III] and/or in combination with another alkylaluminum compound such as trimethylaluminum, triethylaluminum, triisobutylaluminum or dimethylaluminum chloride.

Examples of the ionic compound reactive with Component (A) to convert Component (A) to a cation include those represented by the general formula [V]:

$$[K]^{e+}[Z]^{e-} \qquad [V]$$

wherein K represents an ionic cation component, and examples thereof include carbonium, tropylium, ammonium, oxonium, sulfonium and phosphonium cations. Further examples of the ionic compound include cations of metals and cations of organometals that, as such, are likely to be reduced. Specific examples of these cations include (i) triphenylcarbonium, and diphenylcarbonium, (ii) cycloheptatrienium, and indenium, (iii) triethylammonium, tripropylammonium, tributylammonium, N,N-dimethylanilinium, dipropylammonium, dicyclohexylammonium, (iv) triphenylphosphonium, trimethylphosphonium, tri(dimethylphenyl)phosphonium, and tri(methylphenyl)phosphonium, (v) triphenylsulfonium, (vi) triphenyloxonium, and triethyloxonium, (vii) pyrylium and (viii) a silver ion, a gold ion, a platinum ion, a copper ion, a palladium ion, a mercury ion and a ferrocenium ion.

In the general formula [V], Z is an ionic anion component that is a counter anion (generally in a noncoordination form) against a cation species formed by conversion of Component (A), and examples thereof include organoboron compound anions, organoaluminum compound anions, organogallium compound anions, organophosphorus compound anions, organoarsenic compound anions and organoantimony compound anions.

Specific examples of Z include:

(i) tetraphenylboron, tetrakis(3,4,5-trifluorophenyl)boron, tetrakis(3,5-di(trifluoromethyl)phenyl)boron and tetrakis(3,5-di(t-butyl)phenyl)boron and tetrakis(pentafluorophenyl)boron;

(ii) tetraphenylaluminum, tetrakis(3,4,5-trifluorophenyl)aluminum, tetrakis(3,5-di(trifluoromethyl)phenyl)aluminum, tetrakis(3,5-di(t-butyl)phenyl)aluminum and tetrakis(pentafluorophenyl)aluminum;

(iii) tetraphenylgallium, tetrakis(3,4,5-trifluorophenyl)gallium, tetrakis(3,5-di(trifluoromethyl)phenyl)gallium, tetrakis(3,5-di(t-butyl)phenyl)gallium and tetrakis(pentafluorophenyl)gallium;

(iv) tetraphenylphosphorus and tetrakis(pentafluorophenyl)phosphorus;

(v) tetraphenylarsenic and tetrakis(pentafluorophenyl)arsenic;

(vi) tetraphenylantimony, and tetrakis(pentafluorophenyl)antimony;

(vii) decaborate, undecaborate, carbadodecaborate and decachlorodecaborate.

Examples of the Lewis acid, particularly Lewis acid which can convert Component (A) to a cation, include various organoboron compounds, metal halogen compounds and solid acids. Specific examples thereof include (i) organoboron compounds such as triphenylboron, tris(3,5-difluorophenyl)boron and tris(pentafluorophenyl)boron, (ii) metal halogen compounds such as aluminum chloride, aluminum bromide, aluminum iodide, magnesium chloride, magnesium bromide, magnesium iodide, magnesium chlorobromide, magnesium chloroiodide, magnesium bromoiodide, magnesium chloride hydride, magnesium chloride hydroxide, magnesium bromide hydroxide, magnesium chloride alkoxide and magnesium bromide alkoxide, and (iii) solid acids such as silica-alumina and alumina.

The ionic compound and the Lewis acid may be used as Component (B) alone or in combination therewith or with an aluminum oxy compound represented by the general formula [II], [III] and [IV]. Further, it is also possible to use the ionic compound and the Lewis acid in combination with an organoaluminum compound such as a tri-lower-alkylaluminum, a di-lower-alkylaluminum monohalide, a mono-lower-alkylaluminum dihalide and a lower-alkylaluminum sesquihalide and derivatives of the above-described compounds such that a part of the lower alkyl group has been substituted with a phenoxy group or a halogen atom, for example, trimethylaluminum, triethylaluminum, triisobutylaluminum, diethylaluminum phenoxide and dimethylaluminum chloride.

<Preparation of Catalyst>

The catalyst according to the present invention can be prepared by bringing the above-described Component (A) and Component (B) into contact with each other in the presence or absence of a monomer to be polymerized, inside or outside a polymerization vessel.

The amounts of Components (A) and (B) used in the present invention are not particularly limited. For example, in the case of solvent polymerization, the amount of Component (A) is preferably in the range of from $10^{-7}$ to $10^2$ mmol/liter, still preferably in the range of from $10^{-4}$ to 1 mmol/liter, in terms of the transition metal atom. When use is made of an aluminum oxy compound, the Al/transition metal molar ratio is preferably no lower than 10 and no higher than 100,000, still preferably no lower than 100 and no higher than 20,000, particularly preferably no lower than 100 and no higher than 10,000. When an ionic compound or a Lewis acid is used as Component (B), it is used in an amount in the range of from 0.1 to 1,000, preferably in the range of from 0.5 to 100, still preferably in the range of from 1 to 50, in terms of the molar ratio thereof to the transition metal.

As described above, the catalyst according to the present invention can contain some further component in addition to Components (A) and (B). Examples of the third or optional component which can be added to Components (A) and (B) include compounds containing active hydrogen such as $H_2O$, or an alkanol such as methanol, ethanol and butanol, electron-donating compounds such as ethers, esters and amines, alkoxyl-containing compounds such as phenyl borate, dimethylmethoxyaluminum, phenyl phosphate, tetraethoxysilane and diphenyldimethoxysilane.

When the above catalyst systems are used for the polymerization of olefins, Component (A) and Component (B) may be introduced separately into a reaction vessel or alternatively introduced into a reaction vessel after they are brought into contact with each other. When Components (A) and Component (B) are previously brought into contact with each other, the contact can be effected in the presence of a monomer to be polymerized, thereby polymerizing part of the olefin, i.e., effecting a so-called "preliminary polymerization".

<Use of Catalyst/Polymerization of Olefin>

The catalyst of the present invention is, of course, applicable to slurry polymerization where a solvent is used and also to polymerizations where substantially no solvent is used such as liquid phase, non-solvent polymerization, gas-phase polymerization and solution polymerization. Moreover, the catalyst of the invention can also be applied to continuous polymerization and batch-wise polymerization.

In the case of solvent polymerization, a saturated aliphatic and aromatic hydrocarbon such as hexane, heptane, pentane, cyclohexane, benzene and toluene is used as a solvent. They may be used alone or in combination of two or more thereof.

The polymerization temperature is approximately in the range of from −78° to 200° C., preferably in the range of from −20° to 100° C. There is no particular limitation on the olefin pressure of the reaction system. However, the pressure is preferably in the range of from atmospheric pressure to 50 $kg/cm^2 \cdot G$.

In the polymerization, the molecular weight of the polymer can be controlled by any known method, for instance, by properly selecting the temperature or pressure of the polymerization, or by the introduction of hydrogen.

The α-olefins polymerizable in the presence of the catalyst of the present invention, that is, α-olefins (including ethylene) usable for the polymerization reaction in the process according to the present invention are α-olefins having 2 to 20 carbon atoms, preferably 2 to 10 carbon atoms. Specifically, the catalyst of the present invention is preferably used for the stereoregular polymerization of α-olefins having 3 to 10 carbon atoms such propylene, 1-butene, 4-methyl-1-pentene, 1-hexene, 1-octene, 1-decene, 1-dodecene, 1-tetradecene, 1-hexadecene, 1-octadecene and 1-eicosene, particularly preferably for the polymerization of propylene. A mixture of two or more of these α-olefins can also be used for the polymerization.

The catalyst of the present invention can also be used for the copolymerization of the above-described α-olefins of 3 or more carbon atoms with ethylene. Moreover, the catalyst of the present invention is also useful for the copolymerization of the above α-olefins and other monomers copolymerizable therewith, for example, conjugated and non-conjugated dienes such as butadiene, 1,4-hexadiene, 7-methyl-1,6-octadiene, 1,8-nonadiene and 1,9-decadiene, and various cyclic olefins such as cyclopropene, cyclobutene, cyclopentene, norbornene and dicyclopentadiene.

Following examples illustrate the present invention more specifically but non-limitatively.

[Example 1]

Synthesis of dimethylsilylenebis(2,4,4-trimethyl-4,5,6,7-tetrahydro-4-silaindenyl)zirconium dichloride (1) Methylcyclopentadiene dimer was heated under nitrogen atmosphere, and a fraction boiling at 72° to 80° C. was separated. 25.0 g (0.31 mole) of the fraction was diluted with 300 ml of dried tetrahydrofuran, which will be referred to as THF, and the solution prepared was cooled to −78° C. To the solution was added 195 ml of n-butyllithium in a 1.6 M hexane solution over a period of 1 hour, followed by agitation at room temperature for 1 hour.

The reaction mixture was cooled again to −78° C., and 53.4 g (0.31 mole) of chloro(3-chloropropyl)dimethylsilane dissolved in 50 ml of dried THF was added over a period of 40 minutes. The reaction mixture was agitated at room temperature for 1 hour and then heated under reflux for 6 hours. The reaction mixture was cooled to room temperature and was poured onto 500 g of ice, and the product was subjected to extraction with ether and the extract was dried and concentrated to give 48.8 g of pale yellow liquid, which was identified upon 1H-NMR analysis to be 3-chloropropyl-(4-methylcyclopenta-1,3-dien-2-yl)dimethylsilane (and its isomers in terms of the double bond).

(2) 35.0 g (0.16 mole) of the product obtained in (1) was dissolved in 300 ml of methylethylketone, and the solution, after addition thereto of 48.0 g of sodium iodide, was heated under reflux for 12 hours. The reaction product was subjected to extraction to give 49.8 g of a product which was determined upon $^1$H-NMR analysis to be a 3-iodopropyl product (83.2, triplet).

(3) 30.6 g (0.10 mole) of the product obtained in (2), namely 3-iodopropyl-(4-methylcyclopentadien-2-yl)dimethylsilane, was dissolved in 800 ml of dried THF and agitated at −78° C. 62 ml of n-butyllithium in a 1.6 M hexane solution was added thereto dropwise over a period of 80 minutes, and the mixture was agitated at −78° C. for 1 hour. The reaction mixture was then agitated at room temperature for 1 hour and further 2 hours under reflux.

The reaction mixture was then poured into water and the product was subjected to extraction with ether, and the extract was dried and concentrated to give 17.1 g of a crude product, which was purified by silica gel chromatography (hexane) to give 12.8 g of an oily product. The oily product obtained was identified upon $^1$H-NMR analysis to be 2,4,4-trimethyl-4,5,6,7-tetrahydro-4-silaindenyl.

(4) 11.5 g (64 mmole) of the product obtained in (3) was dissolved in 150 ml of dried THF, and to this solution was added dropwise, under agitation at −78° C., 40.3 ml of n-butyllithium in 1.6 M hexane solution over a period of 30 minutes. The reaction mixture was agitated at room temperature for 1 hour, followed by concentration in vacuo to distill off about 150 ml of volatile components. To the residue in the reaction vessel was added 200 ml of dried toluene, and the mixture was cooled to 0° C. followed by addition thereto of 4.16 g (32 mmoles) of dichlorodimethylsilane. The reaction mixture was heated at 50° C. for 5 hours and then at 100° C. for 6 hours.

The reaction mixture was poured into 200 ml of water, and the organic layer formed was separated and washed with 5% aqueous sodium bicarbonate (50 ml) and water (200 ml×2), dried and concentrated to give 10.9 g of a viscous oily product.

The product was identified upon $^1$H-NMR analysis to be bis[(2,4,4-trimethyl-4,5,6,7-tetrahydro-4-sila)indenyl] dimethylsilane.

(5) 4.00 g (9.7 mmoles) of the product obtained in (4) was dissolved in 200 ml of dried THF, and to this solution was added dropwise, under nitrogen atmosphere at −78° C., 12.1 ml of n-butyllithium in 1.6 M hexane solution over a period of 30 minutes. The reaction mixture was agitated at 0° C. for 1 hour and cooled again to −78° C.

3.66 g of zirconium tetrachloride/THF complex containing 2 molecules of THF per 1 atom of zirconium was dissolved in 100 ml of dried THF, and the solution obtained was added to the reaction mixture prepared above over a period of 30 minutes. The mixture was agitated for 2 hours at −78° C. and further 12 hours at room temperature.

The reaction mixture was concentrated in vacuo, and to the residue obtained which was orange in color was added 250 ml of dried dichloromethane. The mixture obtained was filtered to remove any undissolved matter, and the filtrate was concentrated to give 5.50 g of an orange crystalline solid, which upon recrystallization in a toluene-pentane mixture gave 3.25 g of a pure product.

The product was identified upon 1H-NMR analysis to be dimethylsilylenebis(2,4,4-trimethyl-4,5,6,7-tetrahydro-4-silaindenyl)zirconium dichloride.

Polymerization of propylene

A 1.5-liter agitation-type autoclave was thoroughly purged with propylene. 500 ml of toluene which had been thoroughly dehydrated and deoxygenated was introduced into the autoclave. To the toluene were added 10 mmol (0.58 g) (in terms of Al atom) of methylalumoxane (degree of polymerization: 16) manufactured by Toso-Akzo and 0.573 mg (1 μmol) of the dimethylsilylenebis(2,4,4-trimethyl-4,5,6,7-tetrahydro-4-silaindenyl)zirconium dichloride synthesized above. After propylene was introduced into the mixture, preliminary polymerization was carried out at 20° C. and 1 kg/cm$^2$·G for 15 min. The temperature of the reaction system was raised to 40° C., and polymerization was carried out at that temperature and 7 kg/cm$^2$·G for 2 hr. After the completion of the polymerization, the resultant polymer slurry was filtered to collect a polymer which was then dried to give 42.7 g of a polymer product. The filtrate was concentrated to give 0.4 g of a polymer. The catalytic activity was 75,200 g polymer/g Component (A), and the polymer had a number average molecular weight (Mn) of 28.6×10$^4$, a molecular weight distribution (Mw/Mn) of 2.10 and a melting point (MP) of 157.5° C.

[Example 2]

Polymerization of propylene

Propylene was polymerized as in Example 1, except that the polymerization temperature was 70° C. in place of 40° C. Catalytic activity was 126,500 g/g Component (A), Mn=21.5×10$^4$, Mw/Mn=2.25 and MP=153.1° C.

[Example 3]

Polymerization of propylene

Propylene was polymerized as in Example 1, except that 500 ml of toluene and 139 mg (0.7 mmol) of triisobutylaluminum were introduced, 0.573 mg (1 μmol) of dimethylsilylenebis(2,4,4-trimethyl-4,5,6,7-tetrahydro- 4-silaindenyl)zirconium dichloride was introduced and 1.6 mg (2 μmol) of dimethylanilinium[tetrakis(pentafluorophenyl)borate] was introduced, and preliminary polymerization of propylene was conducted at 20° C. under a propylene pressure of 1 kg/cm$^2$G for 15 minutes.

Propylene was then polymerized at 40° C. under a pressure of 7 kg/cm$^2$G for 2 hours.

The results are given in Table 1.

[Comparative Example 1]

Synthesis of dimethylsilylenebis(tetrahydroindenyl)zirconium dichloride

Dimethylsilylenebis(tetrahydroindenyl)zirconium dichloride was synthesized according to a method described in J. Orgmet. Chem. (342) 21–29 (1988) and J. Orgmet. Chem. (369) 359–370 (1989).

Specifically, a solution of 5.4 g of bis(indenyl)dimethylsilane diluted with 150 ml of tetrahydrofuran was introduced in 300-ml flask purged with nitrogen and cooled to no higher than −50° C., and 23.6 ml of n-butyllithium (1.6 M/liter) was added dropwise over a period of 30 min. After the completion of the dropwise addition, the temperature of the mixture was raised to room temperature over a period of one hr, and a reaction was allowed to proceed at room temperature for 4 hr, thereby synthesizing a reaction mixture A.

200 ml of tetrahydrofuran was introduced into a 500-ml flask purged with nitrogen and cooled to no higher than −50° C., and 4.38 g of zirconium tetrachloride was gradually introduced thereinto. Then, the reaction mixture A was introduced at a time, and the temperature of the mixture was gradually raised to room temperature over a period of 3 hr. A reaction was allowed to proceed at room temperature for 2 hr. The temperature was raised to 60° C., and a reaction was allowed to proceed at that temperature for an additional 2 hr. After the completion of the reaction, the solvent was removed by distillation under reduced pressure. The residue was dissolved in 100 ml of toluene, and the solvent was again removed by distillation to give 3.86 g of a crude crystal of dimethylsilylenebis(indenyl)zirconium dichloride.

Then, the crude crystal was dissolved in 150 ml of dichloromethane, and the solution was introduced into a 500-ml autoclave. After 5 g of platinum-carbon (0.5% by weight platinum supported) catalyst was introduced, a hydrogenation reaction was effected under conditions of H$_2$=50 kg/cm$^2$·G and 50° C. for 5 hr. After the completion of the reaction, the catalyst was removed by filtration, the solvent was removed by distillation under reduced pressure, and the residue was extracted with toluene and then recrystallized to give 1.26 g of dimethylsilylenebis(tetrahydroindenyl)zirconium dichloride as an intended product.

Polymerization of Propylene

Propylene was polymerized as in Example 1, except that Component (A) was used in an amount of 0.456 mg (1 μmol). The results are given in Table 1.

[Comparative Example 2]

Propylene was polymerized as in Comparative Example 1, except that the polymerization temperature was 70° C. The results are given in Table 1.

TABLE 1

| | Component (A) (Amount) | Component (B) (Amount) | | | Polymerization conditions | Catalytic activity (g-polymer/g component (A)) | GPC | | Melting point (°C.) |
|---|---|---|---|---|---|---|---|---|---|
| | | Methylalumoxane | *3 | *4 | | | Mn | Mw/Mn | |
| Ex. | | | | | | | | | |

TABLE 1-continued

| | Component (A) (Amount) | Component (B) (Amount) | | | Polymerization conditions | Catalytic activity (g-polymer/g component (A)) | GPC | | Melting point (°C.) |
|---|---|---|---|---|---|---|---|---|---|
| | | Methylalumoxane | *3 | *4 | | | Mn | Mw/Mn | |
| 1 | *1 1 μmol | 10 mmol | — | — | 40° C. 7K2H | 75,200 | 28.6 × 10⁴ | 2.18 | 157.5 |
| 2 | *1 1 μmol | 10 mmol | — | — | 70° C. 7K2H | 126,500 | 21.5 × 10⁴ | 2.25 | 153.1 |
| 3 | *1 1 μmol | — | 700 μmol | 2 μmol | 40° C. 7K2H | 175,000 | 25.5 × 10⁴ | 2.05 | 158.6 |
| Comp. Ex. | | | | | | | | | |
| 1 | *2 1 μmol | 10 mmol | — | — | 40° C. 7K2H | 223,000 | 3.40 × 10⁴ | 2.15 | 149.3 |
| 2 | *2 1 μmol | 10 mmol | — | — | 70° C. 7K2H | 517,000 | 0.91 × 10⁴ | 1.96 | 118.1 |

*1: Dimethylsilylenebis(2,4,4-trimethyl-4,5,6,7-tetrahydro-4-silaindenyl)zirconium dichloride

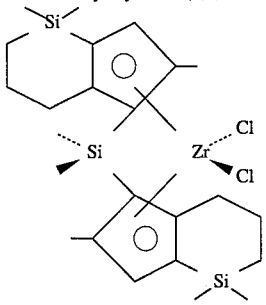

*2: Dimethylsilylenebis(4,5,6,7-tetrahydroindenyl)zirconium dichloride

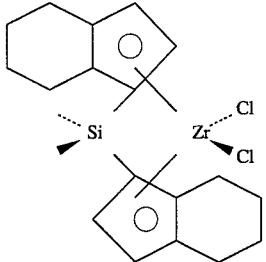

*3: Triisobutylalumoxane
*4: Dimethylanilinium tetrakis(pentafluorophenyl)borate

[Example 4]

Synthesis of dimethylsilylenebis(4,4-dimethyl-4,5,6,7-tetrahydro-4-silaindenyl)zirconium dichloride (1) Cyclopentadiene dimer was heated under nitrogen atmosphere, and a fraction boiling at 41° to 42° C. was separated. 34 g (0.51 mole) of the fraction was added dropwise under nitrogen over a period of 1 hour to 160 ml of dried THF containing 13 g of sodium hydride (purity: 95%, 0.51 mole) dispersed therein, and the dispersion was agitated for 15 hours at room temperature.

To the resultant reaction-mixture was added dropwise at room temperature 89 g (0.52 mole) of chloro(3-chloropropyl)dimethylsilane over a period of 90 minutes, and the mixture was further agitated for 24 hours at room temperature.

The resultant reaction mixture was poured into 500 ml of ice water, and the product was subjected to extraction with ether and the extract was dried and concentrated to give pale yellow liquid, which was purified by silica gel chromatography (eluent: hexane) and then by distillation in vacuo to give 37.5 g of colorless transparent liquid boiling at 70°–75° C./1.5 mmHg.

The product obtained was identified upon ¹H-NMR analysis to be 3-chloropropylcyclopenta-1,3-dien-2-yl)dimethylsilane (and its isomer mixture in terms of the double bond).

(2) 200 ml of dried THF containing 4.4 g of sodium hydride (purity: 95%, 0.18 mole) dispersed therein was cooled to 0° C. under nitrogen, and 35 g (0.17 mole) of the product obtained in (1) above was dissolved in 30 ml of dried THF, and the latter was added dropwise to the former over a period of 30 minutes. The resultant reaction mixture was agitated for 90 minutes at room temperature, and heated for 4 hours under reflux. The reaction mixture was cooled to room temperature and was then poured in 700 ml of ice water, and the product was subjected to extraction with diethylether and the extract was dried and concentrated to give pale yellow liquid, which gave upon distillation in vacuo 7.5 g of colorless transparent liquid boiling at 83° C./23 mmHg.

The product was identified upon ¹H-NMR analysis to be 4,4-dimethyl-4,5,6,7-tetrahydro-4-silaindene.

(3) 7.5 g (45 mmole) of the product obtained in (2) was dissolved in 30 ml of dried THF, and to this solution was added dropwise, under nitrogen at 0° C., 22.2 ml of n-butyllithium in 1.6 M hexane solution over a period of 20 minutes. The reaction mixture was agitated at 0° C. for 30 minutes.

To the resultant reaction mixture was added dropwise at 0° C. 264 mg (20.5 mmole) of dichlorodimethylsilane, followed by agitation for 12 hours at room temperature.

The reaction solvent was distilled off in vacuo, and the resultant residue was dissolved in 100 ml of pentane, followed by washing with saturated aqueous ammonium chloride, drying and concentration to give a crude product, which, upon purification by silica gel chromatography (hexane), gave 2.01 g of pale yellow liquid.

(4) 2.01 g of the product obtained in (3) above was dissolved in 30 ml of dried diethylether, and to this solution was added dropwise under nitrogen at −78° C. 6.3 ml of n-butyllithium in 1.6 M hexane solution over a period of 10 minutes. The mixture was brought to room temperature under agitation over a,period of 13 hours, and the solvent was distilled off in vacuo.

To the resultant residue in the reaction vessel was added 50 ml of dried methylene chloride, and the mixture was cooled to −78° C. followed by addition thereto of 1.14 g (4.8 mmoles) of zirconium tetrachloride. The reaction mixture was gradually brought to room temperature under agitation over a period of 15 hours, and allowed to react for 3 hours at room temperature. The insoluble matters were filtered off and the filtrate was dried into a solid, which, after washing with a small amount of dried toluene, was again dissolved in 30 ml of dried methylene chloride. The resultant solution was concentrated into a volume of 10 ml, and subjected to crystallization at −35° C. over a period of 15 hours. The crystals upon filteration and washing with dried n-hexane gave 0.30 g of dimethylsilylenebis(4,4-dimethyl-4,5,6,7-tetrahydro-4-silaindenyl)zirconium dichloride.

Polymerization of propylene

Propylene was polymerized as in Example 1, except that 1 μmol of dimethylsilylenebis(4,4-dimethyl-4,5,6,7-tetrahydro- 4-silaindenyl)zirconium dichloride.

The results are given in Table 2.

[Example 5]

Polymerization of propylene

Propylene was polymerized as in Example 4, except that the polymerization temperature was changed to 70° C.

The results are given in Table 2.

[Example 6]

A 1.5-liter agitation-type autoclave was thoroughly purged with propylene, and 5 mmoles (2.64 ml), an Al atom basis, of a commercial product of methylalumoxane (MMAO by Toso-Akzo) and 1 μmole of dimethylsilylenebis(4,4-dimethyl- 4,5,6,7-tetrahydro-4-silaindenyl)zirconium dichloride, and 600 ml of liquefied propylene were added thereto. The temperature was raised to 70° C. and polymerization was conducted for 1 hour. Propylene was purged and the polymer was taken out, and dried.

The results are given in Table 2.

[Example 7]

Copolymerization of propylene with 1-hexene

The procedure set forth in Example 4 was followed, except that 30 ml of 1-hexene was introduced after the introduction of 500 ml of toluene.

The results are given in Table 2.

TABLE 2

| Ex. | Component (A) (Amount) | Component (B) (Amount) | Polymerization conditions | Catalytic activity (g-polymer/g component (A)) | GPC Mn | GPC Mw/Mn | Melting point (°C.) | Bulk density (g/c.c.) |
|---|---|---|---|---|---|---|---|---|
| 4 | *1 (1 μmol) | Methyl-alumoxane (10 mmol) | 40° C. 7K2H T*2: 500 ml | 58,000 | 83,000 | 2.25 | 156.5 | 0.27 |
| 5 | *1 (1 μmol) | Methyl-alumoxane (10 mmol) | 70° C. 7K2H T*2: 500 ml | 107,000 | 25,000 | 2.11 | 145.8 | 0.18 |
| 6 | *1 (1 μmol) | MMAO (5 mmol) | 70° C. 30K1H P*3: 600 ml | 225,000 | 48,400 | 2.38 | 150.3 | 0.22 |
| 7 | *1 (1 μmol) | Methyl-alumoxane (10 mmol) | 40° C. 7K2H T*2: 500 ml H*4: 30 ml | 63,000 | 77,000 | 2.12 | 143.8 | 0.18 |

*1: Dimethylsilylenebis(4,4-dimethyl-4,5,6,7-tetrahydro-4-silaindenyl)zirconium dichloride

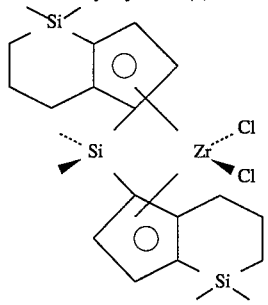

*2: Toluene,
*3: Propylene,
*4: 1-Hexene

[Example 8]

Synthesis of ethylenebis(4,4-dimethyl-4,5,6,7-tetrahydro-4-silaindenyl)zirconium dichloride (1) 4,4-Dimethyl-4,5,6,7-tetrahydro-4-silaindene in an amount of 3.4 g (21 mmol) was dissolved in 2.0 ml of dried THF, to which were added under nitrogen atmosphere and at 0° C. 13.0 ml of n-butyllithium in a 1.66 M hexane solution dropwise over a period of 10 minutes and then 3.6 g (22.0 mmol) of hexamethylphosphoric triamide. The reaction mixture was cooled to −78° C., followed by dropwise addition thereto of 1.3 g (7.0 mmol) of 1,2-dibromoethane. After the addition, the reaction mixture was gradually warmed and was heated under reflux for 10 hours. The reaction mixture was then cooled to room temperature and poured into 100 ml of ice water, whereupon the product was subjected to extraction with diethylether. The extract obtained was dried and concentrated to form a crude product, which, upon purification by silica gel chromatography (hexane), gave 1.4 g of liquid.

(2) The liquid obtained in (1) above in an amount of 1.4 g (4.0 mmol) was dissolved in 10 ml of dried diethylether, to which was added under nitrogen at −78° C. 4.8 ml of n-butyllithium in a 1.66 M hexane solution dropwise over a period of 30 minutes. After the addition, the reaction mixture was warmed to room temperature over a period of 2 hours under agitation, and the solvent was distilled off in vacuo.

To the remaining residue in the reaction vessel were added 20 ml of dried methylene chloride and, upon cooling to −78° C., 0.93 g (4 mmol) of zirconium tetrachloride. The reaction dispersion was gradually warmed to room temperature over a period of 52 hours under agitation, and was allowed to react at room temperature for 12 hours. After the reaction, insolubles were filtered off. The filtrate obtained was dried to solid, the solid obtained was washed with a small amount of dried toluene and was then dissolved in 20 ml of dried methylene chloride. The solution formed was concentrated into 10 ml to precipitate crystals at −20° C. for 15 hours, which were filtered, washed with dried n-hexane and dried, and 0.42 g of ethylenebis(4,4-dimethyl-4,5,6,7-tetrahydro-4-silaindenyl)zirconium dichloride was obtained.

Polymerization of propylene

Propylene was polymerized as in Example 4 except for the use of 1 μmol of the complex obtained above.

The result obtained is set forth in Table 3.

[Example 9]

Propylene was polymerized as in Example 5 except for the use of the complex prepared in Example 8.

The result obtained is set forth in Table 3.

TABLE 3

| | Component (A) (Amount) | Component (B) (Amount) | Polymerization conditions | Catalytic activity (g-polymer/g component (A)) | GPC Mn | GPC Mw/Mn | Melting point (°C.) | Bulk density (g/c.c.) |
|---|---|---|---|---|---|---|---|---|
| Ex. | | | | | | | | |
| 8 | *1 (1 μmol) | Methyl- alumoxane (10 mmol) | 40° C. 7K2H T*2: 500 ml | 22,000 | 27,800 | 3.50 | 151.5 142.3 | 0.15 |
| 9 | *1 (1 μmol) | Methyl- alumoxane (10 mmol) | 70° C. 7K2H T*2: 500 ml | 105,000 | 14,500 | 2.97 | 150.2 140.3 | 0.18 |

*1: Ethylenebis(4,4-dimethyl-4,5,6,7-tetrahydro-4-silaindenyl)zirconium dichloride

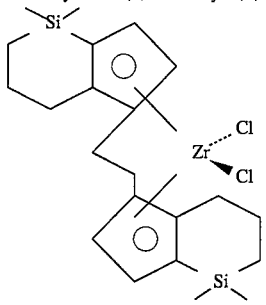

*2: Toluene

What is claimed is:

1. A catalyst component for use in the polymerization of α-olefins which comprises a compound represented by the following formula [I]:

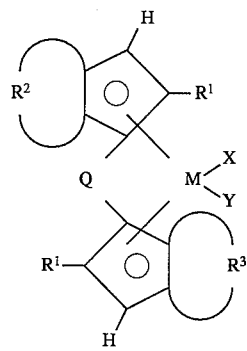

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent group selected from the group consisting of a hydrocarbon group having 3 to 30 carbon atoms and a silicon-containing hydrocarbon group having 1 to 30 carbon atoms and 1 to 6 silicon atoms, provided that at least one of $R^2$ and $R^3$ is said silicon-containing hydrocarbon group; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table.

2. The catalyst component as claimed in claim 1, wherein the metal M in the compound is selected from the group consisting of titanium, zirconium and hafnium.

3. The catalyst component as claimed in claim 2, wherein the metal M is zirconium.

4. The catalyst component as claimed in claim 1, wherein $R^1$ is a hydrogen atom.

5. The catalyst component as claimed in claim 1, wherein $R^1$ is an alkyl group of 1 to 4 carbon atoms.

6. The catalyst component as claimed in claim 1, wherein Q is selected from the group consisting of alkylene, cycloalkylene, arylene and alkylsilylene groups.

7. The catalyst component as claimed in claim 1, wherein Q is selected from the group consisting of an alkylene and an alkylsilylene.

8. The catalyst component as claimed in claim 7, wherein Q is selected from the group consisting of dimethylsilylene and ethylene.

9. The catalyst component as claimed in claim 8, wherein Q is dimethylsilylene.

10. The catalyst component as claimed in claim 8, wherein Q is ethylene.

11. A catalyst for the polymerization of α-olefins which comprises in combination:

Component (A) which is a transition metal compound represented by the formula [I] set forth in claim 1; and Component (B) which is a member selected from the group consisting of an aluminum oxy compound, a Lewis acid and an anionic compound which can react with Component (A) to convert Component (A) to a cation.

12. The catalyst as claimed in claim 11, wherein the aluminum oxy compound of Component (B) is selected from the compounds respectively represented by the formulae:

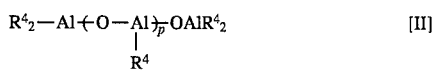  [II]

  [III]

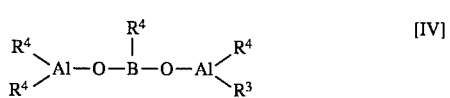  [IV]

wherein p is a number of 0 to 40, $R^4$ is hydrogen, a hydrocarbon group or a halogen-containing hydrocarbon group.

13. A process for producing an α-olefin polymer which comprises contacting an α-olefin of 2 to 20 carbon atoms with a catalyst comprising in combination Component (A) and Component (B) as claimed in claim 11 thereby to polymerize the α-olefin.

14. The process as claimed in claim 13, wherein the α-olefin has 2 to 10 carbon atoms.

15. The process as claimed in claim 14, wherein the α-olefin has 3 to 10 carbon atoms.

16. A catalyst component for use in the polymerization of α-olefins which comprises a compound represented by the following formula [I]:

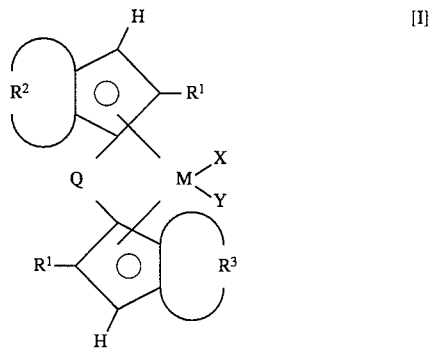

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent group selected from the group consisting of a hydrocarbon group having 3 to 30 carbon atoms and a silicon-containing hydrocarbon group having 1 to 30 carbon atom and 1 to 6 silicon atoms, provided that at least one of $R^2$ and $R^3$ is said silicon-containing hydrocarbon group; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB ti VIB transition metal of the Periodic Table, wherein each of $R^2$ and $R^3$ is the silicon-containing hydrocarbon group wherein the silicon is a member of the ring fused with the five membered ring.

17. The catalyst component as claimed in claim 16, wherein $R^1$ is a hydrogen atom.

18. The catalyst component as claimed in claim 16, wherein $R^1$ is an alkyl group of 1 to 4 carbon atoms.

19. The catalyst component as claimed in claim 16, wherein Q is selected from the group consisting of alkylene, cycloalkylene, arylene and alkylsilylene groups.

20. The catalyst component as claimed in claim 16, wherein Q is selected from the group consisting of an alkylene and an alkylsilylene.

21. The catalyst component as claimed in claim 20, wherein Q is selected from the group consisting of dimethylsilylene and ethylene.

22. The catalyst component as claimed in claim 21, wherein Q is dimethylsilylene.

23. The catalyst component as claimed in claim 21, wherein Q is ethylene.

24. A catalyst for the polymerization of α-olefins which comprises in combination:

Component (A) which is a transition metal compound represented by the formula [I] set forth in claim 16; and Component (B) which is a member selected from the group consisting of an aluminum oxy compound, a Lewis acid and an anionic compound which can react with Component (A) to convert Component (A) to a cation.

25. The catalyst as claimed in claim 24, wherein the aluminum oxy compound of Component (B) is selected from the compounds respectively represented by the formulae:

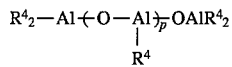   [II]

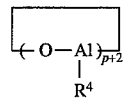   [III]

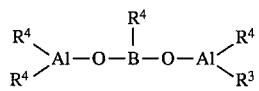   [IV]

wherein p is a number of 0 to 40, $R^4$ is hydrogen, a hydrocarbon group or a halogen-containing hydrocarbon group.

26. A process for producing an α-olefin polymer which comprises contacting an α-olefin of 2 to 20 carbon atoms with a catalyst comprising in combination Component (A) and Component (B) as claimed in claim 24 thereby to polymerize the α-olefin.

27. The process as claimed in claim 26, wherein the α-olefin has 2 to 10 carbon atoms.

28. The process as claimed in claim 27, wherein the α-olefin has 3 to 10 carbon atoms.

29. The catalyst component as claimed in claim 16, wherein the metal M in the compound is selected from the group consisting of titanium, zirconium and hafnium.

30. The catalyst component as claimed in claim 29, wherein the metal M is zirconium.

* * * * *